(12) United States Patent
Sinha et al.

(10) Patent No.: US 6,555,712 B2
(45) Date of Patent: Apr. 29, 2003

(54) PROCESS FOR THE PREPARATION OF DIORGANOTRISULFIDE

(75) Inventors: Pradipta Sinha, Kharagpur (IN); Sujit Roy, Kharagpur (IN)

(73) Assignees: Indian Institute of Technology, Kharagpur (IN); Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/820,202

(22) Filed: Mar. 28, 2001

(65) Prior Publication Data

US 2002/0198410 A1 Dec. 26, 2002

(51) Int. Cl.[7] .............................................. C07C 321/00
(52) U.S. Cl. .............................. 568/21; 568/23; 568/25
(58) Field of Search ............................... 568/21, 22, 23, 568/24, 25

(56) References Cited

U.S. PATENT DOCUMENTS 2,097,155 A * 10/1937 Groll et al.
3,256,328 A *  6/1966 Hauptschein et al.
4,125,552 A * 11/1978 Speier

OTHER PUBLICATIONS

CA:105:225463 abs of JP61126066 Jun. 1986.*
CA:94:15195 abs of JP55047649 Apr. 1980.*
CA:134:162551 abs of Organometallics by Sinha et al 20(1) pp 157–162 2001.*

* cited by examiner

*Primary Examiner*—Jean F. Vollano
(74) *Attorney, Agent, or Firm*—Ladas & Parry

(57) ABSTRACT

The present invention discloses a process for the preparation of a diorganotrisulfide said process by reacting an organic halide and elemental sulfur (α-rhombic) using catalytic copper (II) halide and tin (II) halide in a mixture of organic solvents at 30–70° C.

9 Claims, No Drawings

PROCESS FOR THE PREPARATION OF DIORGANOTRISULFIDE

FIELD OF THE INVENTION

The present invention relates to a process for the preparation of diorganotrisulfides, a class of compounds having proven and potential bioactivity. The invention particularly relates to a catalytic process of preparing diorganotrisulfides in general, and diallyltrisulfides, in particular, from the reaction of elemental sulfur and organic halides in the presence of catalytic copper (II) halide and tin (II) chloride in a mixture of organic solvents.

BACKGROUND OF THE INVENTION

Garlic (*Allium Sativum*) has been used for more than 400 years in traditional medicine against cardiovascular diseases, cancer and various infections. A major sulfur component of fresh garlic is allin (S-2-propenyl-L-Cysteine-S-oxide) which is converted into allicin (diallyl thiosulfinate) upon softening of the bulb. Allicin, upon isolation, is spontaneously degraded to two major compounds, namely Ajoene (4,5,9-triihiadodeca-1,6,11-triene-9-oxide) and diallyltrisulfide (DATS). Extensive research has shown that both these compounds show very high bioactivity [S Fukushima, N Takada, T Hori & H Wanibuchi. J Cell Biochem. Suppl., 27. pp. 100–5 (1997)].

Diallyltrisulfide (DATS) is a highly bioactive agent and is domestically marketed in China since 1981, by the name DASUANSU, for treatment of bacterial, fungal and parasitic infections in man. Recent research has conclusively proved its bioefficacy. For example, the activity of DATS was investigated in several important protozoan parasites in vitro [Z.R. Lun, C. Burri, M. Menzinger & R. Kaminsky. Ann. Soc. Belg. Med. Trop., 74:1 pp. 51–9 (1994)]. The IC50 (concentration which inhibits metabolism or growth of parasites by 50%) for *Trypanosoma brucei brucei, T.b. rhodesiense, T.b. gambiense, T. evansi, T. congolense* and *T. equiperdum* was in the range of 0.8–5.5 micrograms/ml. IC50 values were 59 micrograms/ml for *Entamoeba histolytica* and 14 micrograms/ml for *Giardia Lamblia*. The cytotoxicity of the compound was evaluated on two fibroblast cell lines (MASEF, *Mastomys natalensis* embryo fibroblast and HEFL-12, human embryo fibroblast) in vitro. The maximum tolerated concentration for both cell lines was 25 micrograms/ml. The results indicate that DATS has potential to be used for treatment of several human and animal parasitic diseases. Inhibition of whole blood platelet-aggregation by DATS, present in the steam-distilled component of garlic extract was also found to be high [L. D. Lawson, D. K. Ransom & B. G. Hughes. Thromb. Res., 65:2. Pp. 141–56 (1992)]. Oil-soluble organosulfur compounds from Garlic, notably DATS, markedly inhibits the growth of canine mammary tumor cells (CMT-13). The inhibitory effect was also found to be modified by intracellular glutathione [S. G. Sundaram & J. A. Milber. Cancer Lett., 74:1–2, pp. 85–90 (1993)]. Results from the in-vitro study of antiproliferative effects of DATS on cultured human neoplastic (A549) and nonneoplastic (MRC-5) lung cells is quite encouraging [K Sakamoto, L. D. Lawson & J. A. Milber. Nutr. Cancer, 29:2, pp. 152–6 (1997)]. Addition of 10 micromolar Data reduced A549 growth by 47%. DATS treatment (10 microM) did not alter MRC-5 cell growth. DATS (10 microM) caused a marked and progressive increase in intracellular $Ca^{2+}$ in A549 cells during the first four hours after treatment. Intracellular $Ca^{2+}$ in A549 cells exposed to DATS returned to near control levels within one hour after refeeding the medium without DATS. Exposure to 1 microM DATS for 24 hours significantly induced apoptosis, as indicated by increased DNA fragmentation. The ability of DATS to suppress neoplastic growth is consistent with increasing evidence that several garlic components have anticarcinogenic and antitumorigenic properties. Studies on the effect of DATS on the activation of T cell and macrophage-mediated cytotoxicity suggest that DATS may be potentially useful in tumor therapy [Z. H. Feng, G. M. Zhang, T. L. Hao, B. Zhou, H. Zhang & Z. Y. Jiang, J. Tongji Med. Uni., 14;3 pp. 142–7 (1994)]. At high concentration (50 micrograms/ml), DATS had an inhibitory effect on T cell activation. But at appropriate concentrations (3.125–12.5 micrograms/ml), DATS augmented the activation of T lymphocytes by Con A. The augmentation of T cell activation by DATS was related to its inhibitory effect on the production of nitric oxide (NO) by macrophages. In a wide range of concentrations (1–100 micrograms/ml), DATS can inhibit the production of NO by macrophages. In addition, DATS can antagonize the inhibition of tumor derived immunosuppressive factors produced by S180 cells and Ehrlich ascitic cancer cells on the activation of T cells, and reduce the inhibitory rate significantly. DATS, despite its inhibition of the production of NO by macrophages, can also enhance the production of hydrogen peroxide ($H_2O_2$) by macrophages. DATS and related sulfides were also tested against *Sitophilus zeamais* (Motschulsky) and *Tribolium castaneum* (Herbst) for contact toxicity, fumigant toxicity, and antifeedant activity [Y. Huang, S. X. Chen & S. H. Ho., J. Econ. Entomol., 93:2 pp. 537–43 (2000)]. For adults of these two species of insects, the contact and fumigant toxicities of DATS was greater than that of methylallyl disulfide. These two compounds were also more toxic to *T. castaneum* adults than to *S. Zeamais* adults. Older *T. castaneum* larvae were more susceptible to the contact toxicity of the two compounds, whereas younger larvae were more susceptible to the fumigant toxicity of these compounds. Both compounds reduced egg hatching of *T. castaneum* and subsequent emergence of progeny. DATS totally suppressed egg hatching at 0.32 mg/ck2, and larval and adult emergence at 0.08 mg/cm2. Methylallyl disulfide significantly decreased the growth rate, food consumption, and food utilization of adults of both insect species, with feeding deterrence indices of 44% at 6.08 mg/g food for *S. zeamais* and 1.52 mg/g food for *T. castaneum*. However, it did not affect any nutritional indices of *T. castaneum* larvae. On the other hand DATS significantly reduced all of the nutritional indices in all of the insects tested. Feeding deterrence indices of 27 and 51% were obtained in *S. zeamais* adults and *T. castaneum* larvae, respectively, at the concentration of 2.98 mg/g food, whereas feeding deterrence of 85% was achieved in *T. castaneum* adults at a much lower concentration of 0.75 mg/g food. Hence, DATS is a more potent contact toxicant, fumigant and feeding deterrent than methylallyl disulfide. Finally, the spermicidal effect of some of the active principles of Garlic was found to be quite positive [Y. X. Qian, P. J. Shen, R. Y. Xu, G. M. Liu, H. Q. Yang, Y. S. Lu, P. Sun, R. W. Zhang, L. M. Qi & Q. H. Lu, Contraception. 34:3. Pp. 295–302 (1986). The inhibition of sperm motility was found to be concentration dependent and range from 20 seconds 200 minutes.

In spite of their importance, a straight forward, high yielding, catalytic and cost effective process for the preparation of diorganotrisulfide in general and diallyltrisulfide (DATS), in particular is yet to achieve. One of the most common preparative route for diorganotrisulfides involves the reaction of highly corrosive sulfur dichloride (s2Cl2) with organothiol at 0° C. [D. N. Harpp & R. A. Smith. J. Org. Chem., 44 pp. 4140 (1979); G. Derbesy & D. N. Harpp. Tetrahedron Lett., 35 pp. 5381 (1994)]. A major disadvantage of the process is the formation of by product such as disulfide, tetrasulfide. The shelf life of sulfurdichloride is very limited as a result of its tendency to decompose to element sulfur, chlorine gas and series of homologous sulfur dichlorides [D. N. Harpp., K. Steliou & T. H. Chan. J. Am. Chem. Soc., 100 pp. 1222 (1978); Q. E. Thompson. J. Org. Chem., 30. Pp. 2703 (1965)], which in turn leads to the formation of diorganopolysulfides and requiring multistage distillation for purification prior to every process. Notwithstanding the said difficulties, the main drawback of using sulfurdichloride is its eco-unfriendliness and serious process hazard due to its corrosive nature. As a result of the above, new sulfur-transfer agents have been developed [D. N. Harpp., K. Steliou & T. H. Chan. J.Am. Chem. Soc., 100. pp. 1222 (1978); A. Banerji & G. P. Kalena. Tetrahedron Lett., 21. Pp. 3003 (1980)], which react with organothiols giving rise to diorganotrisulfides. It is important to note that such specialty sulfur-transfer regents are prepared in multistep and often use sulfurdichloride. Furthermore organic thiols are themselves hazardous to health.

Morel et al had earlier reported a single example for the preparation of DATS from the reaction of sulfur with 18 equivalent of potassium hydroxide and 8 equivalent of allyl bromide, the product being obtained in only 30% yield [G. Morel, E. Marchand & A. Foucaud. Synthesis, pp. 918 (1980)].

OBJECTS OF THE INVENTION

The main object of the present invention, therefore is to provide a catalytic, cost effective and eco-friendly process for the preparation of diorganotrisulfides, in general, and diallytrisulfide (DATS) in particular.

It is another object of the invention to provide a catalytic process for the preparation of diorganotrisulfides in general and diallyltrisulfides in particular which results in good yield of the desired product.

SUMMARY OF THE INVENTION

The invented catalytic process described herein meets all the stipulations targetted above. For example, in the invented catalytic process, readily available starting materials such as allyl halide, copper (II) chloride, tin (II) chloride and elemental α-rhombic sulfur are used.

Accordingly the present invention relates to a process for the preparation of a diorganotrisulfide said process comprising reacting an organic halide and elemental sulfur (α-rhombic) using catalytic copper (II) halide and tin (II) halide in a mixture of organic solvents at 30–70° C. and isolating the desired diorganotrisulfide.

In one embodiment of the invention, the organic halide is selected from the group consisting of allyl halides, alkyl (C1–C6) halides, benzyl halides and 4-substituted benzyl halides.

In one embodiment of the invention, the organic halide used is selected from the group consisting of allyl bromide, 1-bromo-2-butene, 1-bromo-2-hexene, cinnamyl bromide, methyl iodide, benzyl iodide and 4-nitrobenzyl bromide.

In one embodiment of the invention, the copper (II) halide used is selected from the group consisting of anhydrous copper (II) chloride, copper (II) chloride dihydrate and copper (II) bromide.

In one embodiment of the invention, the weight proportion of catalytic copper (II) halide used is in the range of 5–20 mol % with respect to organic halide.

In another embodiment of the invention, the tin (II) halide used is selected from anhydrous tin (II) chloride and tin (II) chloride dihydrate.

In a further embodiment of the invention, the weight proportion of tin (II) halide is in the range of 1.02 to 1.2 equivalent with respect to organic halide.

In another embodiment of the invention, the organic solvent mixture used comprises a mixture of dimethylsulfoxide and tetrahydrofuran in a ratio from 1:1 to 1:2 volume/volume.

DETAILED DESCRIPTION OF THE INVENTION

In the process of the invention, Diorganotrisulfides are prepared from the reaction of organic halide with tin (II) chloride, catalytic copper (II) halide and elemental α-rhombic sulfur, in a mixture of organic solvents. Organic halides refer to primary alkyl (C1 to C6), benzyl, substituted benzyl, allyl bromides and corresponding iodides. When the organic halide is in particular an allyl halide, the allyl group refers to substituted allyls, where the substitution is at the 3-position of the allyl group, and the substituents can be an alkyl (C1 to C6), or aryl group. The copper halide can be anhydrous copper (II) chloride, copper (II) chloride dihydrate or copper (II) bromide. Tin halide can be anhydrous tin (II) chloride or tin (II) chloride dihydrate. The mixture of organic solvents refers to a mixture of dimethylsulfoxide and tetrahydrofuran in a ratio from 1:1 to 1:2 volume/volume. The reaction temperature can be 30–70° C. The product diorganotrisulfide is isolated by adding an aqueous solution of ammonium fluoride to the reaction mixture, extracting the organic product with diethyl ether and finally by column chromatography and/or by distillation.

Thus, addition of elemental sulfur (α-rhombic, 100 g-atom) to a mixture of tin (II) chloride dihydrate (13.54 g, 60 mmol) and catalytic copper (II) chloride dihydrate (1.7 g, 10 mmol) in tetrahydrofuran-dimethylsulfoxide (2:1 volume/volume) leads to the immediate formation of a brown colored precipitate. Addition of allyl bromide (8.5 ml, 76 mmol) to this mixture at 70° C. results in a clear yellow solution after 2h. Work-up chromatography, followed by distillation afforded DATS 1 (boiling point 50C/0.07 torr) in 51% isolated yield, with a overall conversion of 78% with respect to halide (Table 1, entry 1). A small amount of diallyltetrasulfide is also detected (vide NMR) in the product mixture, prior to distillation. It is important to note that the catalytic reaction proceeds equally well with copper (II) bromide as the catalyst. The pronounced effect of copper catalyst in the transformation can be judged from the fact that no reaction occurs either in absence of copper salts or in the presence of nickel chloride, bis(triphenylphosphine) nickel dichloride, palladium acetate, and tetrakis (Triphenylphosphine) palladium as catalysts. Negligible product is formed with copper (II) halide/tin(II) halide in solvents such as dichloromethane, acetonitrile, tetrahydrofuran, dichloromethane-dimethylsulfoxide (2:1 volume/volume), and acetonitrile-dimethylsulfoxide (2:1 volume/volume).

The invented process, described above for DATS, is further extended to various allyl (Table 1, entry 3–5), 1-alkyl (entry 6,7) and benzyl (entry 8,9) halides given rise to the corresponding diorganotrisulfides 2–7 in moderate to excellent conversions. However the reaction fails in the case of aryl halides. It is observed that reactions also proceed at room temperature but the rates of the reaction are slower (entry 2,7). This indicates the inherent reactivity of the reagent in promoting diorganotrisulfide formation. All products described herein were fully characterized by $^1$H NMR (500 MHz), mass spectral analyses, elemental analyses and comparison with authentic samples where ever possible.

The details of the invention are given in the examples provided below which are given for illustration only and should not be construed to limit the scope of the present invention.

Table 1: Preparation of Diorganotrisulfides $R_2S_3$ from the reaction of organic halide RX and Elemental Sulfur using Catalytic Copper (II) Halide & Tin(II) Chloride$^a$.

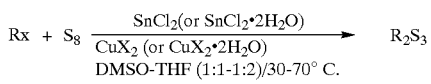

TABLE 1

| # | RX | Temp (° C.) | Time (h) | Pdt. No. | Conversion (%)$^b$ | Isolated Yield (%) |
|---|---|---|---|---|---|---|
| 1 | $CH_2$=$CHCH_2Br$ | 70 | 2 | 1 | 78 | 51 |
| 2 | $CH_2$=$CHCH_2Br$ | 30 | 10 | 1 | 45 | 31 |
| 3 | $CH_3CH$=$CHCH_2Br$ | 70 | 1 | 2 | 72 | 30 |
| 4 | $C_3H_7CH$=$CHCH_2Br$ | 60 | 5 | 3 | 33 | 17 |
| 5 | $C_6H_5CH$=$CHCH_2Br$ | 50 | 9 | 4 | 42 | 20 |
| 6$^c$ | MeI | 50 | 1 | 5 | 53 | 36 |
| 7$^d$ | MeI | 30 | 12 | 5 | 32 | 21 |
| 8 | $C_6H_5CH_2I$ | 30 | 12 | 6 | 48 | 22 |
| 9 | $4$-$NO_2C_6H_5CH_2Br$ | 35 | 12 | 7 | 26 | 17 |

$^a$Unless otherwise stated, copper (II) halide used is $CuCl_2.2H_2O$, tin(II) chloride used is $SnCl_2.2H_2O$
$^b$Conversion with respect to halide vide $^1$H NMR and GC
$^c$$CuBr_2$ is used
$^d$Anhydrous $CuCl_2$ and $SnCl_2$ is used

EXAMPLE 1

Preparation of Diallyltrisulfide 1 at 70° C.

Sulfur (3.2 gm, 100 g-atom) was added to a stirred solution containing tin (II) chloride dihydrate (13.54 gm, 60 mmol) and copper (II) chloride dihydrate (1.7 gm, 10 mmol) in dimethylsulfoxide-tetrahydrofuran (1:2 volume/volume). Allyl bromide (8.5 ml, 75 mmol) was added dropwise to the reaction mixture kept under argon. The solution was stirred at 70° C. for 2 hr. An aqueous solution of ammonium fluoride (15%, 200 ml) was added to the reaction mixture, organic layer was extracted with diethyl ether (5×200 ml), washed with water (2×500ml), brine (2×500 ml) and dried over magnesium sulfate. Solvent removal followed by distillation afforded DATS 1 (4.54 gm, 51%). $^1$H NMR ($CDCl_3$) δ (ppm): 3.58 (2H), 5.91 (1H, m), 5,25 (2H, m); EIMS m/z (rel abundance): 178 (5), 146 (17), 114 (6), 81 (19), 64 (79), 41 (100); Anal ($C_6H_{10}S_3$) calcd., C:40.45, H: 5.62; found, C: 39.82, H: 55.

EXAMPLE 2

Preparation of Diallyltrisulfide 1 at 30° C.

Sulfur (3.2 gm, 100 g-atom) was added to a stirred solution containing tin(II) chloride dihydrate (13.54 gm, 60 mmol) and copper (II) chloride dihydrate (1.7 gm, 10 mmol) in dimethylsulfoxide-tetrahydrofuran (1:2 volume/volume). Allyl bromide (8.5 ml, 75 mmol) was added dropwise to the reaction mixture kept under argon. The solution was stirred at 30° C. for 10 hr. An aqueous solution of ammonium fluoride (15%, 200 ml) was added to the reaction mixture, organic layer was extracted with diethyl ether (5×200 ml), washed with water (2×500 ml), brine (2×500 ml) and dried over magnesium sulfate. Solvent removal followed by distillation afforded DATS 1 (2.76 gm, 31%). $^1$H NMR ($CDCl_3$) δ (ppm): 3.58 (2H), 5.91 (1H, m), 5,25 (2H, m); EIMS m/z (rel abundance): 178 (5), 146 (17), 114 (6) 81 (19), 64 (79), 41 (100).

EXAMPLE 3

Preparation of Di (2-butenyl)trisulfide 2 at 70° C.

Sulfur (3.2 gm, 100 g-atom) was added to a stirred solution containing tin (II) chloride dihydrate (11.85 gm, 52.5 mmol) and copper (II) chloride dihydrate (850 mg, 5 mmol) in dimethylsulfoxide-tetrahydrofuran (1:2 volume/volue). 1-bromo-2-butene (7.5 ml, 75 mmol) was added dropwise to the reaction mixture kept under argon. The solution was refluxed at 70° C. for 1 hr. An aqueous solution of ammonium fluoride (15%, 200 ml) was added to the reaction mixture, organic layer was extracted with diethyl ether (5×200 ml), washed with water (2×500 ml), brine (2×500 ml) and dried over magnesium sulfate. Solvent removal followed by column chromatography (silica gel 100–200 mesh) afforded a viscous oil Di(2-butenul) trisulfide 2. (3.09 gm, 30%). $^1$H NMR ($CDCl_3$) δ (ppm): 3.54 (2H), 1.73 (3H, d) 5.7 (1H, m), 5.52 (1H, m); EIMS m/z (rel abundance): 206 (12), 174 (19), 141 (8), 64 (52), 55 (100); Anal ($C_8H_{14}S_3$) calcd, C:46.60, H:6.79; found, C:45.92, H:6.53.

EXAMPLE 4

Preparation of Di (2-hexenyl)trisulfide 3 at 60° C.

Sulfur (3.2 gm, 100 g-atom) was added to a stirred solution containing tin (II) chloride dihydrate (11.85 gm, 52.5 mmol) and copper (II) chloride dihydrate (850 mg, 5 mmol) in dimethylsulfoxide-tetrahydrofuran (1:1.7 volume/volume). E-1-bromohex-2-ene (8.15 gm, 50 mmol) dissolved in the same mixture of solvent was added dropwise to the reaction mixture kept under argon. The solution was refluxed at 60° C. for 5 hr. An aqueous solution of ammonium fluoride (15%, 500 ml) was added to the reaction mixture, organic layer was extracted with diethyl ether (3×800 ml), washed with water (2×500 ml), brine (2×500 ml) and dried over magnesium sulfate. Solvent removal followed by column chromatography (Silica gel 100–200 mesh) afforded a viscous oil Di (2-hexenyl)trsifulfide 3(2.23 gm, 17%). $^1$H NMR ($CDCl_3$) δ (ppm): 3.54 (2H), 0.92 (3H, t), 1.42 (2H, m), 2.04 (2H, m), 5.67 (1H, m); EIMS m/z (rel abundance): 262 (3), 230 (19), 198 (4), 83 (89), 64 (62); Anal ($C_{12}H_{22}S_3$) calcd, C: 54.96, H:8.39; found, C: 54.01, H:8.03.

EXAMPLE 5

Preparation of Di (3-phenyl-2-propenyl)trisulfide 4 at 50° C.

Sulfur (3.2 gm, 100 g-atom) was added to a stirred solution containing tin (11) chloride dihydrate (11.85 gm, 52.5 mmol) and copper (II) chloride dihydrate (850 mg, 5 mmol) in dimethylsulfoxide-tetrahydrofuran (1:2 volume/volume). Cinnamyl bromide (10.35 gm, 52.5 mmol) dissolved in the same mixture of solvent was added dropwise to the reaction mixture kept under argon. The solution was refluxed at 50° C. for 9 hr. An aqueous solution of ammonium fluoride (15%, 200 ml) was added to the reaction mixture, organic layer was extracted with diethyl ether (5×200 ml), washed with water (2×500 ml), brine (2×500 ml) and dried over magnesium sulfate. Solvent removal followed by column chromatography (silica gel 100–200 mesh) afforded a viscous oil Di(3-phenyl-2-propenyl) trisulfide 4 (3.3 gm, 20%). $^1$H NMR (CDCl$_3$) δ (ppm): 3.73 (2H), 6.22 (1H, m), 6.56 (1H, m), 7.3 (5H, m); EIMS m/z (rel abundance): 330 (2), 298 (3), 266 (13), 233(4), 117 (100), 103 (17), 77 (28); Anal (C$_{18}$H$_{18}$S$_3$) calcd, C: 65.45, H: 5.45; found, C: 64.91, H: 5.20.

EXAMPLE 6

Preparationof Dimethyltrisulfide 5 at 50° C.

Sulfur (3.2 gm, 100 g-atom) was added to a stirred solution containing tin (II) chloride dihydrate (11.85 mg, 52.5 mmol) and copper (II) bromide (1.1 gm, 5 mmol) in dimethylsulfoxide-tetrahydrofuran (1:1 volume/volume). Methyl iodide (5ml, 75 mmol) was added dropwise to the reaction mixture kept under argon. The solution was refluxed at 50° C. for 1 hr. An aqueous solution of ammonium fluoride (15%, 200 ml) was added to the reaction mixture, organic layer was extracted with diethyl ether (5,×200 ml), washed with water (2×500 ml), brine (2×500 ml) and dried over magnesium sulfate. Solvent removal followed by column chromatography (silica gel 100–200 mesh) afforded a viscous oil Dimethyltrisulfide 5 (2.27 gm, 36%). $^1$H NMR (CDCl$_3$), δ (ppm): 2.58 (3H); EIMS m/z (rel abundance): 126 (100), 94 (11), 64 (61), 61 (5); Anal (C$_2$H$_6$S$_3$) calcd, C:19.05, H:4.76; found, C:18.88 (11), 64 (61), 61(5); Anal (C2H6S3) calcd, C;19.05, H;4.76; found, C:18.88, H:4.62

EXAMPLE 7

Preparation of Di (benzyl)trisulfide 6 at 30° C.

Sulfur (3.2 gm, 100 g-atom) was added to a stirred solution containing tin (II) chloride dihydrae (11.85 gm, 52.5 mmol) and copper (II) chloride dihydrate (850 mg, 5 mmol) in dimethylsulfoxide-tetrahydrofuran (1:2 volume/volume). Benzyl iodide (10.9 gm, 50 mmol) dissolved in the same mixture of solvent was added dropwise to the reaction mixture kept under argon. The solution was refluxed at 30° C. for 12 hr. An aqueous solution of arnmonium fluoride (15%, 200 ml) was added to the reaction mixture, organic layer was extracted with diethyl ether (5×200 ml), washed with water (2×500 ml), brine (2×500 ml) and dried over magnesium sulfate. Solvent removal followed by column chromatography (Silica gel 100–200 mesh) afforded a viscous oil Di (benzyl) trisulfide 6 (3.06 gm, 22%). $^1$H NMR (CDCl$_3$) δ (ppm): 4.0 (2H), 7.3 (5H, m); EIMS m/z (rel abundance): 280 (0.5), 246 (10), 214 (48), 181 (4), 91 (100), 77 (14); Anal (C$_{14}$H$_{14}$S$_3$) calcd, C: 60.43, H:5.04; found, C:59.90, H:4.82.

EXAMPLE 8

Preparation of Di (4-nitrobenzyl)trisulfide 7 at 35° C.

Sulfur (3.2 gm, 100 g-atom) was added to a stirred solution containing tin (II) chloride dihydrate (11.85 mg, 52.5 mmol) and copper (II) chloride dihydrate (850 mg, 5 mmol) in dimethylsulfoxide-tetrahydrofuran (1:2, volume/volume). 4-nitro benzyl bromide (10.8 gm, 50 mmol) dissolved in the same mixture of solvent was added dropwise to the reaction mixture kept under argon. The solution was refluxed at 35° C. for 12 hr. An aqueous solution of ammonium fluoride (15%, 200 ml) was added to the reaction mixture, organic layer was extracted with diethyl ether (5×200 ml), washed with water (2×500 ml), brine (2×500 ml) and dried over magnesium sulfate. Solvent removal followed by column chromatography (Silica gel 100–200 mesh) afforded a viscous oil Di(4-nitrobenzyl) trisulfide 7 (3.13 gm, 17%). $^1$H NMR (CDCl$_3$) δ (ppm): 4.06 (2H), 7.4 (2H, m), 8.2 (2H, m); EIMS m/z (rel abundance): 368 (1), 336 (8), 304 (19), 272 (9), 136 (100), 121 (26), 77 (42); Anal (C$_{14}$H$_{14}$S$_3$) calcd, C:45.65, H:3.26; found, C:45.25, H:3.09.

We claim:

1. A process for the preparation of a diorganotrisulfide comprising (a) reacting an organic halide and elemental sulfur in the presence of a catalytic copper (II) halide and a tin (II) halide in a mixture of organic solvents at 30–70° C. to form the diorganotrisulfide, wherein the elemental sulfur is α-rhombic elemental sulfur, and (b) isolating the diorganotrisulfide.

2. A process as claimed in claim 1, wherein the organic halide is selected from the group consisting of an allyl halide, and alkyl (C1–C6) halide, a benzyl halide and a 4-substituted benzyl halide.

3. A process as claimed in claim 2, wherein the organic halide is selected from the group consisting of allyl bromide, 1-bromo-2-butene, 1-bromo-2-hexene, cinnamyl bromide, methyl iodide, benzl iodide and 4-nitrobenzyl bromide.

4. A process as claimed in claim 1, wherein the copper (II) halide is selected from the group consisting of anhydrous copper (II) chloride, copper (II) chloride dihydrate and copper (II) bromide.

5. A process as claimed in claim 1, wherein the mole proportion of the catalytic copper (II) halide is in the range of 5–20 mol % with respect to the organic halide.

6. A process as claimed in claim 1, wherein the tin (II) halide is selected from the group consisting of anhydrous tin (II) chloride and tin (II) chloride dihydrate.

7. A process as claimed in claim 1, wherein the weight proportion of tin (II) halide is in the range of 1.02 to 1.2 with respect to the organic halide.

8. A process as claimed in claim 1, wherein the organic solvent mixture comprises a mixture of dimethylsulfoxide and tetrahydrofuran in a ratio from 1:1 to 1:2 volume/volume.

9. A process as claimed in claim 1, (wherein allyl bromide and elemental α-rhombic sulfur are reacted in the presence of catalytic copper (II) chloride dihydrate and tin (II) chloride dihydrate in a mixture of dimethylsulfoxide and tetrahydrofuran at 30–70° C. to form diallyltrisulfide (DATS).

* * * * *